United States Patent
Nolot

(10) Patent No.: US 7,692,782 B2
(45) Date of Patent: Apr. 6, 2010

(54) METHOD FOR FABRICATING HAZE NOISE STANDARDS COMPRISING NANO-STRUCTURES ON AN INSULATING THIN LAYER

(75) Inventor: Emmanuel Nolot, Crolles (FR)

(73) Assignee: Commissariat a l'Energie Atomique, Paris (FR)

(*) Notice: Subject to any disclaimer, the term of this patent is extended or adjusted under 35 U.S.C. 154(b) by 512 days.

(21) Appl. No.: 11/490,071

(22) Filed: Jul. 21, 2006

(65) Prior Publication Data
US 2007/0019188 A1    Jan. 25, 2007

(30) Foreign Application Priority Data
Jul. 22, 2005    (FR) .................... 05 52284

(51) Int. Cl.
*G01J 1/10*    (2006.01)
(52) U.S. Cl. .................. 356/243.4; 356/243.1
(58) Field of Classification Search ......... 356/445–446, 356/242.1, 243.1, 243.4; 438/680, 260, 594, 438/962, 263–264
See application file for complete search history.

(56) References Cited

U.S. PATENT DOCUMENTS

| 5,076,691 A | 12/1991 | Tullis et al. |
| 5,198,869 A | 3/1993 | Monteverde et al. |
| 5,599,464 A | 2/1997 | Laird et al. |
| 6,201,601 B1 | 3/2001 | Vaez-Iravani et al. |
| 6,271,916 B1 | 8/2001 | Marxer et al. |
| 6,784,103 B1 | 8/2004 | Rao et al. |

FOREIGN PATENT DOCUMENTS

JP    63-144242    6/1988

OTHER PUBLICATIONS

Frank Holsteyns, et al., "Monitoring and Qualification Using Comprehensive Surface Haze Information", IEEE International Symposium on Semiconductor Fabrication, 2003, pp. 378-381.
F. Mazen, et al., "A two steps CVD process for the growth of silicon nano-crystals", Applied Surface Science, vol. 214, 2003, pp. 359-363.
R. Brüggemann, et al., "Thickness dependence of optical scattering and surface roughness in microcrystalline silicon", Thin Solid Films, vol. 427, 2003, pp. 358-361.

*Primary Examiner*—Gregory J Toatley, Jr.
*Assistant Examiner*—Tri T Ton
(74) *Attorney, Agent, or Firm*—Oblon, Spivak, McClelland, Maier & Neustadt, L.L.P.

(57) ABSTRACT

Method for the fabrication of Haze noise standards having, respectively, an insulating thin layer and a plurality of nano-structures of hemi-spherical form on the insulating thin layer, with the respective standards being fabricated by: the formation on at least one insulating layer of seeds made of a first semi-conductor material by chemical deposition from a first precursor gas for the first semi-conductor material, formation on the insulating layer of nano-structures based on a second semi-conductor material and in the form of hemi-spheres, from stable seeds of the first semi-conductor material, by chemical deposition from a second precursor gas of the second semi-conductor material. The invention also relates to a calibration method using standards obtained by means of such a method.

13 Claims, 4 Drawing Sheets

METHOD FOR FABRICATING HAZE NOISE STANDARDS COMPRISING NANO-STRUCTURES ON AN INSULATING THIN LAYER

TECHNICAL FIELD

The invention relates to the field of microelectronics and in particular to a method for fabricating haze noise standards, each with a plurality of nano-structures resting on an insulating thin layer. The invention also relates to a calibration method using several standards for equipment designed to measure and/or use haze noise information.

PRIOR ART

During the fabrication method for microelectronic devices such as chips, integrated circuits or MEMS (micro-electromechanical systems) in order to ensure the quality of the device, one or more steps for checking particulate contamination and/or deffect detection steps are usually performed. These checks and/or detection steps are quasi-systematic and may be carried out using equipment designed for optical locating and/or counting of deffects on a thin layer, for example using an image or a photo-multiplier signal. In order to check the quality of a thin layer, such equipment may also carry out measurements of characteristic parameters of the surface of this thin layer, such as, for example, its quadratic roughness or its correlation length.

In performing an analysis of a thin layer, the aforementioned equipment may use a method comprising:
  illuminating the thin layer using one or more light sources,
  carrying out a measurement of the light diffused and diffracted by this thin layer, and using information obtained from a low frequency component of the diffracted or diffused light signal, called "diffuse background noise" or "haze noise" or "haze".

FIG. 1 shows a signal 10 from a measurement carried out by particulate contamination measurement equipment, obtained, for example, using the DWO channel (Dark Wide Field Channel Open Oblique Incidence) of an SP1$^{DLS}$ instrument from the KLA Tencor company. This signal 10 is made up of three components:
  intensity peaks 18 which are greater than a detection limit 16. These peaks are due to the diffraction of the incident laser light on defects in the thin layer such as particles, crystalline defects, scratches etc.
  measurement noise (quasi-random variations in amplitude, shown as 12),
  a low frequency component 14, called haze noise or haze.

Equipment which uses the haze noise information may be calibrated using one or more standards in the form of plates or "wafers" on which patterns of predetermined size are formed, designed to imitate or reproduce the defects in a thin layer.

The document U.S. Pat. No. 5,198,869 shows a haze noise standard device, designed for use in particular in calibrating optical scanners for thin layer inspection systems. This standard includes a plate on which a network of patterns has been made in the form of pits distributed in a quasi-random manner.

Document U.S. Pat. No. 5,599,464 in turn shows various types of haze noise standards formed using photolithography, etching or chemical attack. These standards are in the form of silicon plates which bear patterns of very small dimensions, for example of the order of 10 Angstroms, in particular in the form of convex bumps or grooves, intended to imitate the roughness in a silicon plate after polishing.

The aforementioned standards generally only allow narrow haze noise level ranges to be obtained, for example less than 0.1 ppm for DWO channels in SP1$^{DLS}$ equipment. The problem arises in finding new haze noise standards which allow the entire dynamic range of particulate contamination measurement equipment and deffect detection equipment to be covered, as well as finding a method for the fabrication of such standards.

PRESENTATION OF THE INVENTION

The invention relates to a method for the fabrication of at least one haze noise standard having at least one thin insulating layer and a plurality of nano-structures of hemi-spherical form on the insulating thin layer, comprising steps for:
  a) on at least one insulating layer the formation of 'seeds' of a first semi-conductor material by chemical deposition with a first gas which acts as a precursor for the first semiconductor material,
  b) formation of nano-structures based on a second semi-conductor material on the insulating layer starting from the stable seeds of the first semi-conductor material, by chemical deposition with a second gas acting as a precursor of the second semi conductor material.

Such a method allows standards to be obtained which possess nano-structures which are regularly distributed over an insulating layer. Such a method may also allow standards to be obtained which comprise nano-structures which are of identical or have homogeneous size on an insulating layer. Such a method may also allow a large range of different standards to be obtained in terms of the size of nano-structures that these standards respectively comprise, and provide access through this wide range to an extended accessible or measurable haze noise range.

According to one possibility, step a) may be carried out over a period of exposure to the first precursor gas which is selected to give the predetermined density of seeds which is desired on the insulating layer.

The density of nano-structures may be, for example, between $10^{10}$ nano-structures/$cm^2$ and $5*10^{11}$ nano-structures/$cm^2$.

According to one method of production, step b) may be carried out over a period of exposure to the second precursor gas which is selected to give a predetermined desired size or size range of nano-structures.

The nano-structures may have sizes of between 2 and 50 nanometers.

In one variant, the second precursor may be different to the first precursor.

In one specific application, the first semi-conductor material and the second semi-conductor material may be the same.

The first standard and the second standard may have been exposed to the second gas during step b) for a first period and for a second period respectively, with the first period having been selected to give at least one first predetermined value of haze noise or at least one first predetermined range of haze noise that the first standard is intended to measure, with the second period having been chosen to give at least one second predetermined haze noise value or at least one second predetermined range of haze noise that the second standard is intended to measure.

The invention also relates to a method for fabricating several haze noise standards which includes: the fabrication of at least one first standard and of at least one second standard, with the first standard and the second standard having equal densities of nano-structures, with the first standard comprising nano-structures of a first size or associated with a first range of sizes, and with the second standard comprising nano-structures of a second size which is different to the first size or which is associated with a second range of sizes which is different to the first range.

During step a) the first standard and the second standard may have been placed at the same time and over the same period in the same reactor or in the same deposition chamber, with the first standard and the second standard having been respectively formed at step b) by exposure to the second precursor gas for a first period and by exposure to the second precursor gas for a second period which is different to the first period.

The invention also relates to a calibration method for equipment designed to use and/or measure haze noise value using several standards obtained using a fabrication method as described above.

The invention also relates to a calibration method for equipment designed to use and/or measure a haze noise value comprising steps which consist of:
   providing at least one standard obtained using the method for fabricating standards as defined above,
   emitting at least one type of light radiation towards the nano-structures of at least one standard,
   after this emission, measuring at least one haze noise value using at least one ray which is diffracted or diffused by the standard.

The invention also relates to a haze noise standard device which includes: at least one insulating thin layer and a plurality nano-structures, which have a hemi-spherical or convex bump shape, regularly distributed over the insulating layer.

BRIEF DESCRIPTION OF THE DIAGRAMS

The present invention will be better understood by reading the description of examples of fabrication, which are given for purely informative purposes and which are in no way limitative, whilst referring to the appended diagrams in which.

Identical, similar or equivalent parts of the various figures bear the same numerical references so as to facilitate moving from one figure to another.

In order to make the figures more readable, the various parts represented in the figures are not necessarily shown on a uniform scale.

DETAILED DESCRIPTION OF PARTICULAR EMBODIMENTS

One example of the method for producing a haze noise standard in accordance with the invention will now be described in association with FIGS. 2A-2E.

Figure 2A:
FIGS. 2A-2E show different steps of a method according to the invention for producing a haze noise standard microelectronic device.

The starting material for the method may be a support covered with an insulating thin layer, for example a layer of tunnel dielectric. This starting material may be formed from a substrate 100, which may be a semi-conductor, for example a silicon based semi-conductor, on which a thickness of thermal oxide is made to grow whose thickness is between 1 and 10 nanometers for example, so as to form the thin insulating layer 102 (FIG. 2A). The substrate 100 may, for example, be of silicon<100> with a resistivity of between 7 and 10 $\Omega$.m and P doped.

A step in which the surface roughness of the substrate 100 and/or of the thin insulating layer 102 is checked may perhaps be included. This check may be carried out using an AFM ("Atomic Force Microscopy") measurement. The substrate 100 preferably has a quadratic roughness of less than 0, 5 nanometers. The thin insulating layer 102 preferably has a quadratic roughness of less than 0, 5 nanometers. A cleaning step of the layer 102 may then be carried out in order to remove and/or prevent the formation of organic contaminants. This step may be carried out, for example, using chemical cleaning by means of an aqueous ozone bath followed by rinsing in deionised water, or by passage through an oven at a temperature of around 230° C. for a period, for example, of about 4 minutes.

Then over two periods, or as two distinct steps, a plurality nano-structures are formed on the insulating layer 102.

The term "Nano-structures" is used to mean elements whose size is less than 50 nanometers, for example with a size of between 2 and 50 nanometers. The nano-structures may have convex bump or hemi-spherical shapes. The "size" of the nano-structures refers to the diameter of the base of said hemi-spheres. The nano-structures may be formed, for example, based on at least one semi-conductor material. The nano-structures may be, for example, crystalline elements and in this case will be known as nano-crystals.

The support or substrate 100 covered by the thin insulating layer 102 may be first of all placed in an LPCVD ("Low Pressure Chemical Vapour Deposition") reactor.

Then a first chemical deposition or CVD step is first of all carried out, which is also known as the "nucleation phase". At the end of this nucleation phase, stable seeds of a first semi-conductor material are formed in the form of islands resting on the insulating layer 102 and which are regularly distributed over this layer 102. The term "stable seeds" means that they are not undergoing growth or that growth has been stopped.

Figure 2B:
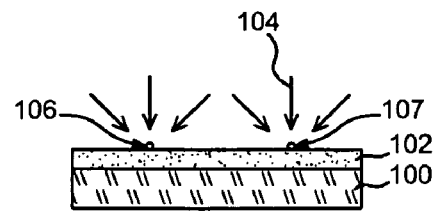

During this first step, a first precursor gas 104 is passed into the interior of the reactor onto the substrate 100 covered with the dielectric layer 102, and this gas allows the seeds 106, 107 to form on the insulating layer 102. The seeds 106, 107 may be based on a first semi-conductor material. The terms "seeds" refers to masses of a few tens to several thousands of atoms. The size of the masses may be very small in relation to that of the final nano-structures that it is wanted to be obtained. The first precursor 104 is selected so that the insulating material 102 can accept the formation of said seeds 106, 107. The first precursor 104 may, be, for example, silane, in order to form seeds 106, 107 based on silicon (FIG. 2B). The first precursor 104 may possibly be diluted in a vector gas.

Preferentially, the dielectric material in the layer 102 is selected so that it is as reactive as possible towards the first precursor 104 of the first semi-conductor layer and so as to favour the formation of seeds rather than the diffusion of the precursor over the surface of the dielectric material in the layer 102. The dielectric material may be, for example, $SiO_2$. The exposure of the dielectric layer 102 to the first precursor gas 104 is performed at a temperature which is sufficient to allow the precursor of the silicon to dissociate and engender the formation of crystalline seeds 106, 107. The deposition temperature may also be selected to be as low as possible in order to limit the speed of growth of the seeds. For example, in the case of silane as the silicon precursor, the formation of silicon seeds may be carried out at a temperature of between 550° C. and 650° C. A low partial pressure of the silicon precursor may be selected in order that the speed of growth of the seeds 106, 107 may be slow. In the case of silane used as the silicon precursor, the partial pressure of silane may be between 35 mTorr and 200 mTorr, for example between 40 m Torr and 80 m Torr.

The deposition time may be selected according to the desired density of seeds for the standard microelectronic device. A slow growth of seeds 106, 107 may be used in order to obtain improved control over the size of the seeds. The time during which the layer 102 is exposed to the first precursor gas may, for example, be between 40 seconds and 200 seconds. The exposure time to the first precursor gas may be short, for example between 40 seconds and 80 seconds, in order to obtain a low surface density of seeds.

The seed density may also be controlled by the chemical properties of the surface of the oxide layer 102. The density of seeds formed during the first step determines the final density of the nano-structures. Thus the final spatial density of the nano-structures that it is desired to obtain on the layer 102 is adjusted during the first step. The conditions for the first deposition may be adjusted so as to obtain a surface density of seeds on the layer 102 which is between $10^{10}$ seeds/$cm^2$ and $5*10^{11}$ seeds/$cm^2$; for example of the order of $5*10^{10}$ seeds/$cm^2$. The step for formation of stable seeds of a first semi-conductor material is carried out over a period or an exposure time which is selected according to the desired seed density, so that the longer the exposure time of the layer 102 to the first precursor 104, the greater the density of seeds 106, 107.

At the end of the first step, stable seeds are obtained on the insulating layer 102, regularly distributed and at a chosen density.

Figure 2C:
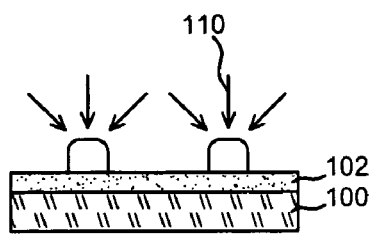

Then during a second step which is distinct from the first step and which is called the "growth phase", the seeds 106, 107 are exposed to a second precursor gas 110. Nano-structures based on a second semi-conductor material will grow selectively on germs 106, 107 formed during the first step (FIG. 2C). The first and second semi-conductor materials may be the same, and based, for example, on silicon.

The second precursor 110 is selected so as to engender selective deposition of the second semi-conductor material only on said seeds 106, 107. The second precursor gas 110 is preferably different to the first precursor gas 104. The fact that two different precursor gases 104 and 110 are used for the first and second step means that one hand the density of nano-structures can be controlled and on the other hand that nano-structures of uniform size are obtained. The second precursor gas 110 may, for example, be dichlorosilane or $Si_2H_2Cl_2$, especially in the case where the formation of nanostructures based on silicon is desired.

The deposition time during the second step is selected depending on the size of nanostructures that it is wanted to obtain. During the second step, the size of nano-structures can be controlled by the deposition conditions, in particular the pressure, the temperature and the duration of this second deposition step. The method conditions that are preferably selected are such that the speed of growth of nano-structures is slow, for example less than 1.2 nanometers per minute, in order to allow the size of said nano-structures to be controlled with a greater degree of precision. A low partial pressure of the second precursor of the first material and a low deposition temperature, but one which allows dissociation to occur at the surface of the dielectric layer 102, are selected. The temperature of the second deposition may be between 550° C. and 670° C., for example between 630° C. and 670° C. The partial pressure of the second precursor may, for example, be between 35 mTorr and 200 mTorr, or for example between 40 mTorr and 80 mTorr.

Figure 2D:
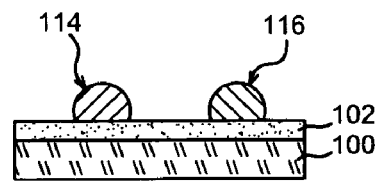

The duration of the second step may be, for example, between 150 and 2000 seconds. Using this method comprising two distinct steps, a standard is obtained which is made up of a support 100, together with a dielectric layer 102 which has a surface of nano-structures 114, 116 of identical or effectively identical sizes or of homogenous sizes on the dielectric layer 102, distributed in a uniform or effectively uniform manner (FIG. 2D). Because the nucleation and growth steps of the method are separated into the two deposition steps described above:

the distribution of nano-structures 114, 116 on the insulating layer 102 obtained using this method is very regular;

the size distribution of nano-structures 114, 116 may be small, for example, less than 30%. By using a first silane-based precursor in the first step and a dichlorosilane-based precursor in the second step, this size distribution may be less than 20%.

The density of nano-structures 114, 116 in the standard may be, for example, between $10^{10}$ nano-structures/$cm^2$ and $5*10^{11}$ nano-structures/$cm^2$, for example of the order of $5*10^{10}$ nano-structures/$cm^2$. The nano-structures 114, 116 in the standard may have sizes between, for example, 2 and 30 nanometers.

Figure 2E:
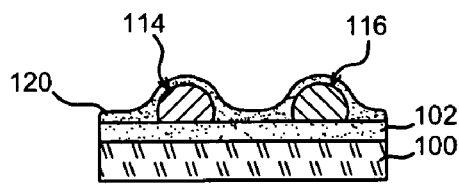

An encapsulation layer 120 for the nano-structures 114, 116, may also be formed (FIG. 2E). The encapsulation layer 120 is preferably formed based on a material which is transparent or of low absorbance towards light radiation. The encapsulation layer 120 is preferably produced so as to completely cover the nano-structures 114, 116. The encapsulation layer 120 may have a thickness of, for example, between 3 and 50 nanometers and may be based on dielectric material such as, for example, $SiO_2$ or $Si_3N_4$. The encapsulation layer 120 may have a protective role and may help preserve nano-structures 114 and 116 from wear and deterioration. The thickness of encapsulation layer 120 and the material(s) from which this layer 120 is formed may be selected so that this layer 120 contributes very little towards the haze measurements and/or may be easily cleaned. The encapsulation layer 120 may be used to stabilise the surface finish roughness formed by the underlying nano-structures.

A check of the effective surface density of the nano-structures 114 and 116 using scanning electron microscopy may be used to refine the method parameters for the first deposition step. Similarly, a check on the size of the nano-crystals using scanning electron microscopy and/or transmission electronic microscopy may allow the duration of the second deposition step to be optimised.

Using a method such as described previously, a wide range of different standards may be obtained. This method may be used to obtain a set or assembly of several standards wherein each respective standard comprises identical nano-structure densities and homogenous nano-structure sizes, and which differ between said standards.

An assembly or set of several haze noise standards E1, E2, E3, E4, and E5 implemented in accordance with a method such as described above is shown in FIG. 3. These standards E1, E2, E3, E4 and E5 are formed on different supports and respectively bear nano-structures $214_1$, $214_2$, $214_3$, $214_4$ and $214_5$ in the form of hemi-spheres, resting respectively on a first thin insulating layer 202 and respectively coated or encapsulated by a second thin insulating layer 220. Between themselves the standards E1, E2, E3, E4 and E5 have identical or effectively identical respective nano-structure densities, for example between $1*10^{10}$ nano-structures/cm² and $5*10^{11}$ nano-structures/cm², of the order, for example, of $5*10^{10}$ nano-structures/cm². In order to form standards E1, E2, E3, E4, and E5 respectively bearing identical densities of nano-structures $214_1$, $214_2$, $214_3$, $214_4$ and $214_5$, the deposition conditions in the nucleation phase and in particular the duration of the nucleation phase can be chosen to be identical for all standards E1, E2, E3, E4, E5. According to one possibility, in order to obtain identical respective nano-structure densities between structures E1, E2, E3, E4 and E5, these may have advantageously been formed during the same nucleation phase in the same reactor or in the same deposition chamber over the same duration period of exposure to the first precursor gas.

In the set of standards, a first standard E1 comprises a first plurality of nano-structures $214_1$, of a first size D1 or associated with a first size range.

A second standard E2 comprises a second plurality of nano-structures $214_2$, of a second size D2 which differs from the first size D1, or is associated with a second size range which is different to the first range.

A third standard E3 comprises a third plurality of nano-structures $214_3$, of a third size D3 which differs from D1 and from D2, or which is associated with a third size range which is different to the first range and the second range.

A fourth standard E4 comprises a fourth plurality of nano-structures $214_4$, of a fourth size D4 which differs from D1 and from D2 and from D3, or which is associated with a fourth size range which is different to the first range and to the second range and to the third range.

A fifth standard E5 comprises a fifth plurality of nano-structures $214_5$, of a fifth size D5 which differs from D1 and from D2 and from D3 and from D4, or which is associated with a fifth size range around the fifth size D5 which is different to the first, second, third and fourth ranges.

According to one possibility, in order to obtain different sizes of nano-structures between standards E1, E2, E3, E4 and E5, then during the growth phase the first standard, the second standard, the third standard, the fourth standard and the fifth standard may have been formed separately and/or with different effective durations of exposure to the second precursor gas.

Such a set of standards E1, E2, E3, E4 and E5 may be used during the calibration method for an item of equipment designed to measure haze noise and which uses measured haze noise information. Because of the range of nano-particle sizes it comprises, such a set of standards can be used to calibrate the aforementioned equipment over a wide dynamic range or over a wide range of haze noise, for example between 0.03 and 300 ppm for the DWO channel of an SP1$^{DLS}$ instrument.

Figure 1:
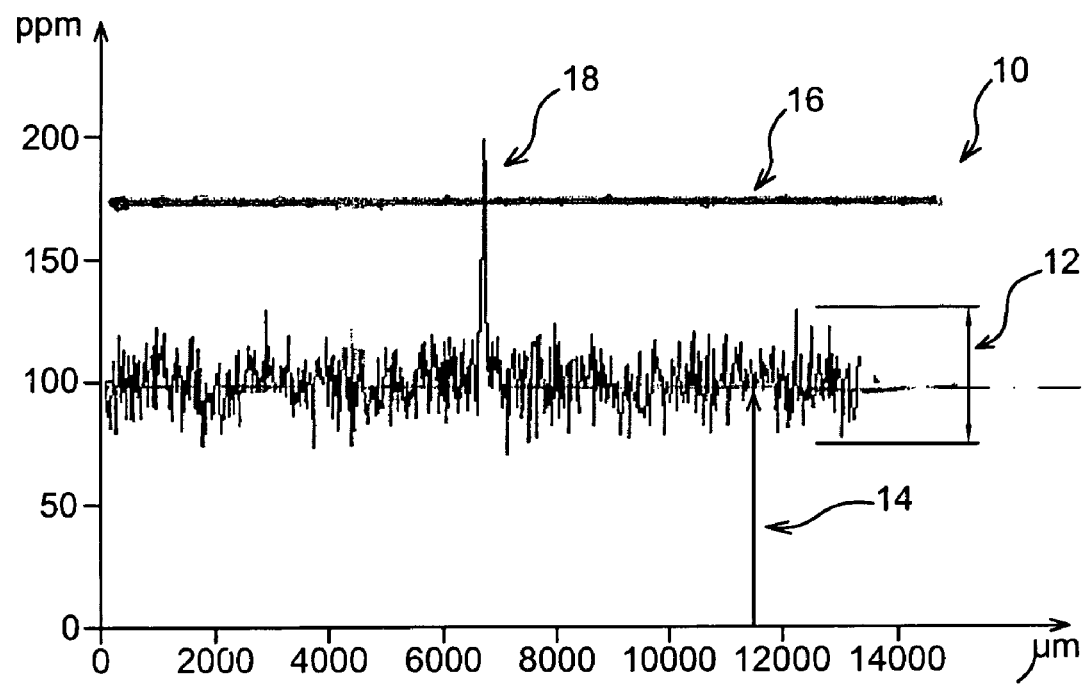
FIG. 1 shows a haze noise measurement signal.
Figure 4:
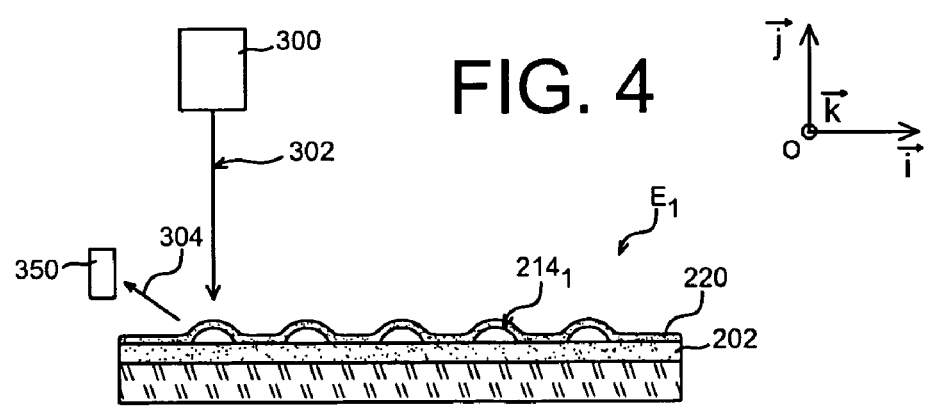
FIG. 4 shows a calibration method with the help of a standard which is used according to the invention and which includes nano-structures regularly distributed over an insulating layer.

FIG. 4 shows a calibration method for equipment designed to measure and use at least one item of information or at least one haze noise measurement, using a set of standards as described earlier in association with FIG. 2.

During this method, a first standard E1 is placed under a beam of light rays 302 emitted by a source 300, for example a laser source. The relative dimensions of the incident beam and the nanostructures are such that several nano-structures of the standard E1 are illuminated by the beam 302. The standard may be made to rotate about itself at, for example, a speed of 4000 rpm. The beam illuminating the standard E1 may, for its part, move along a spiral trajectory.

Figure 3:
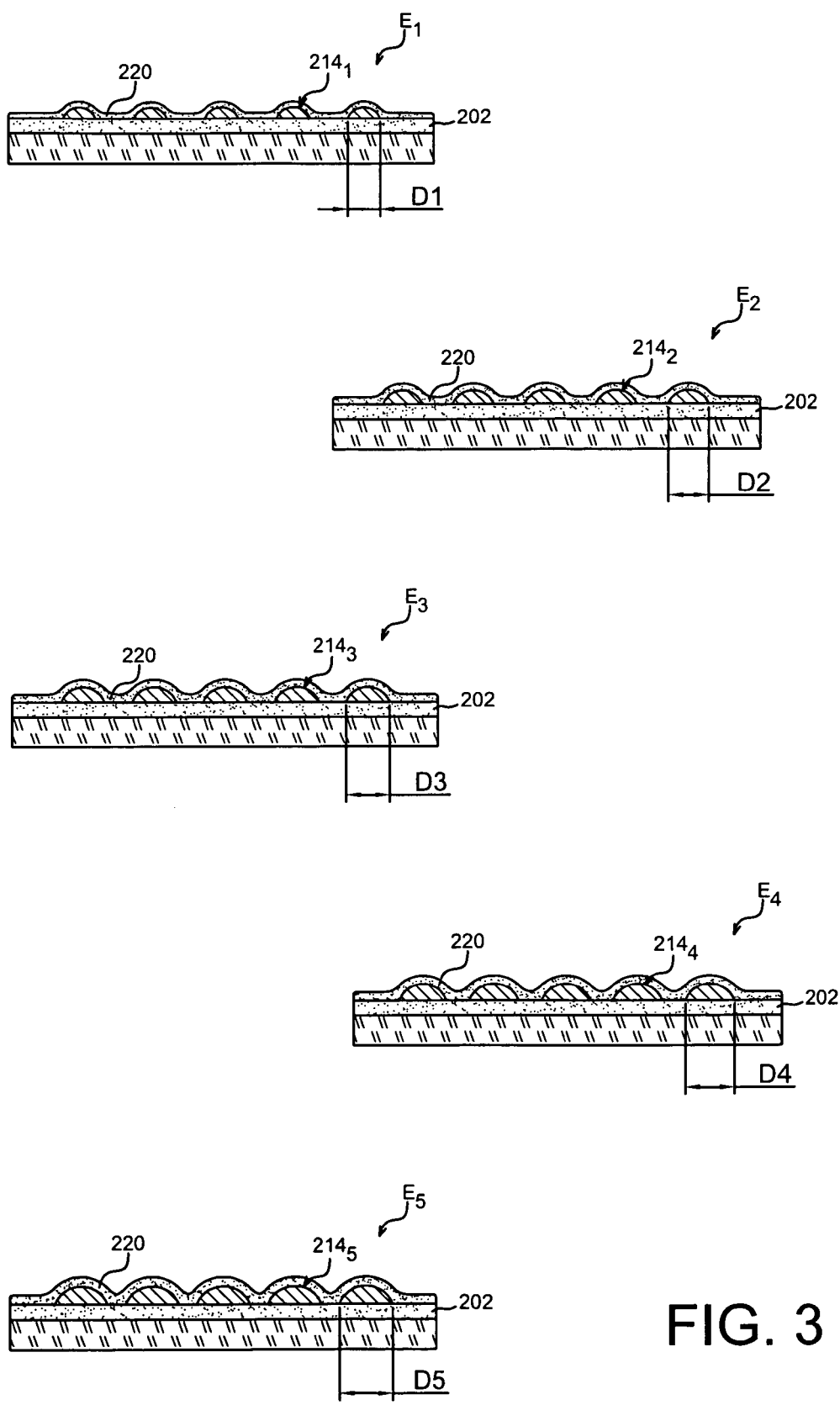
FIG. 3 shows an assembly of several haze noise standards which include nano-structures regularly distributed over an insulating layer, with the nano-structures having different sizes from one standard to another and identical or effectively identical sizes within the same standard.

The beam 302 may make a non-zero angle, for example between 0° and 85°, with a normal to the principal plane (the principal plane of the insulating layer 202 being defined by a direction parallel to a vector at$[0;\vec{i};\ \vec{k}]$ of an orthogonal location$[0;\ \vec{i}\ ;\ \vec{j}\ ;\vec{k}]$ on FIG. 3) of the insulating layer 202 on which nano-structures $214_1$ are arranged. One or more light rays 304 which are diffused or diffracted by the nanostructures $214_1$ are collected by a detector 350. From the light signal received by the detector 350, a low frequency component is extracted which corresponds to a haze noise or "haze" measurement, as is described in the document<<Monitoring and qualification using comprehensive surface haze information>>, Holsteyns et al., IEEE International Symposium on Semiconductor Fabrication, 2003, p 378-381. The result of this measurement is then used as a first reference value.

Multiple measurements can then be made at different points or on different zones on the sample. The dispersion of these multiple haze noise measurements may be less than or equal to 30%.

The method may then be reiterated using the second standard E2, the third standard E3, the fourth standard E4 and the fifth standard E5 in order to obtain a second, third, fourth and then a fifth reference value.

Such measurements may be used to carry out calibration, monitor drift and compare measurement performances of equipment which uses haze noise and/or surface roughness information, such as in equipment for measuring the surface roughness of thin layers, for detecting of defects made in thin layers, particle counters, atomic force microscopes and mechanical profile meters. Such measurements may be used to carry out calibration, monitor drift or compare measurement performance of equipment used for detecting defects as described in the document U.S. Pat. No. 6,201,601 and U.S. Pat. No. 6,271,916 or, for example, SP1$^{DLS}$ equipment fabricationd by the KLA Tencor company.

Figure 5A:
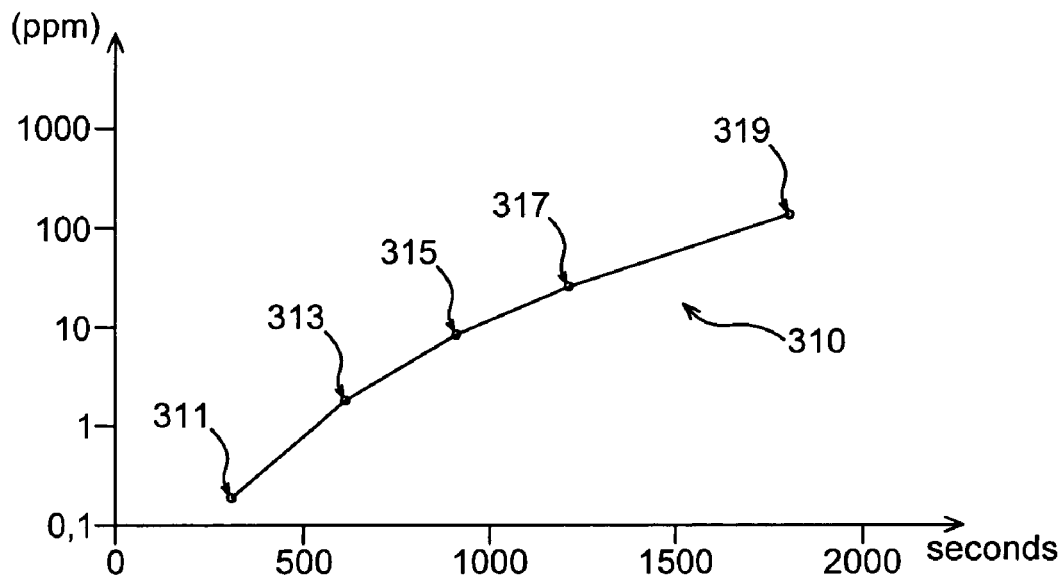
FIG. 5A illustrates, for haze noise standards formed using the method in accordance with invention, the relationship between the period over which the second deposition step or growth phase for these respective standards has taken place, and a haze noise level that is measurable or accessible using these respective standards.

In FIG. 5A, the graph 310 represents haze noise levels as a function of the duration of the second step in the method for fabrication of the standards.

This graph 310 illustrates in particular a dependency or relationship for each haze noise standard between the duration of the second step or growth phase for this standard and a background noise value which is measurable or accessible using this standard. Points 311, 313, 315, 317 and 319 on this graph 310 respectively represent: A haze noise value that is measurable or accessible by measurement using the first standard E1, a haze noise value that is measurable or accessible by measurement using the second standard E2, a haze noise value that is measurable or accessible by measurement using the third standard E3, a haze noise measurement that is measurable or accessible by measurement using the fourth standard E4 and a haze noise value that is measurable or accessible by measurement using the fifth standard E5.

During the fabrication of a given sample from amongst E1, E2, E3, E4 or E5, the duration of the second step may have been chosen as a function of the predetermined haze noise value or range of haze values that this sample is intended to measure. The duration of the second step may have been chosen as a function of the predetermined haze noise value or range of haze noise values that it is desired to access through measurements using this given sample.

Figure 5B:
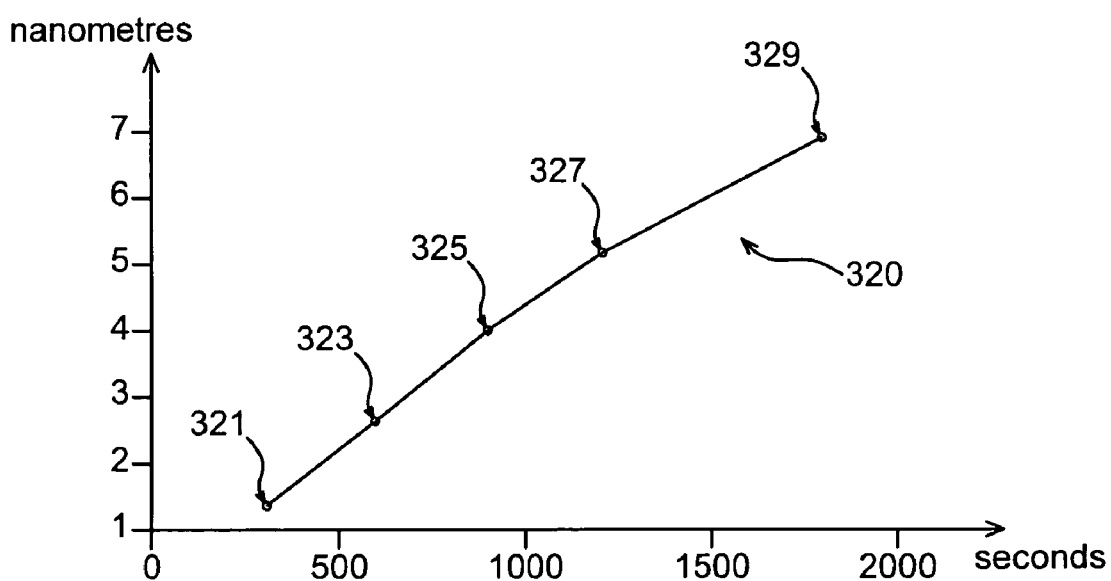
FIG. 5B illustrates, for haze noise standards formed using the method in accordance with invention, the relationship between the period over which the second deposition step or growth phase has taken place for these respective standards, and the level of quadratic roughness which is measurable or accessible using these respective standards.

In FIG. 5B, the graph 320 represents quadratic surface roughness value as a function of the duration of the second step or the growth phase. This graph 320 illustrates the dependency or relationship for each haze noise standard between the duration of the second deposition step or growth phase for this standard, and a quadratic surface roughness value measurable or accessible using this standard. Points 321, 323, 325, 327 and 329 on this graph 320 respectively represent: A quadratic surface roughness value that is measurable or accessible using the first standard E1, a quadratic surface roughness value that is measurable or accessible using the second standard E2, a quadratic surface roughness value that is measurable or accessible using the third standard E3, a quadratic surface roughness value that is measurable or accessible using the fourth standard E4 and a quadratic surface roughness value that is measurable or accessible using the fifth standard E5.

During the fabrication of a given sample from amongst E1, E2, E3, E4 and E5 the duration of the second step may have been chosen as a function of the predetermined haze noise values or of a range of diffuse quadratic surface roughness values that this sample is intended to measure.

The haze noise values of graphs 310 and 320 may have been obtained using equipment for the detection of defects, for example using the SP1 equipment of the KLA Tencor organisation, and in particular using the DWO channel (Dark Field Wide Channel Oblique Incidence).

The invention claimed is:

1. Method for fabricating several Haze noise standards which comprise an insulating thin layer and a plurality of nano-structures which respectively have a hemi-spherical or convex bump shape and which are regularly distributed over the insulating layer comprising the fabrication of at least one first standard and at least one second standard respectively, by a method comprising:
   a) the formation on at least one insulating layer of seeds made of a first semi-conducting material by chemical deposition from a first precursor gas for the first semi-conductor material,
   b) formation on the insulating layer of nano-structures based on a second semi-conductor material, from stable seeds of the first semi-conductor material by chemical deposition from a second precursor gas for the second semi-conductor material,
   wherein the first standard and the second standard have equal densities of nano-structures, with the first standard comprising nano-structures of a first size or associated with a first range of sizes and with the second standard comprising nano-structures of a second size which is different from the first size or associated with a range of sizes which is different from the first range.

2. Method according to claim 1, with the first standard and the second standard having been placed during a), at the same time and over the same period in the same reactor or in the same deposition chamber, with the first standard and the second standard having been respectively formed at b) by exposure to the second precursor gas for a first period and by exposure to the second precursor gas for a second period which is different to the first period.

3. Method according to claim 1, with the first standard and the second standard having been exposed to the second gas during b) for a first period and for a second period respectively, with the first period having been selected depending on at least one first predetermined first value of Haze noise or at least one first predetermined range of Haze noise that the first standard is intended to measure, with the second period having been chosen depending on at least one predetermined second Haze noise value or at least one predetermined second range of Haze noise that the second standard is intended to measure.

4. Method for fabricating at least one Haze standard which comprises an insulating thin layer and a plurality of nano-structures which respectively have a hemi-spherical or convex bump shape and which are regularly distributed over the insulating layer, comprising:
   a) the formation on at least one insulating layer of seeds made of a first semi-conducting material by chemical deposition from a first precursor gas for the first semi-conductor material, a) being carried out over a period of exposure to the first precursor gas which is selected according to the predetermined density of seeds that it is desired to obtain on the insulating layer,
   b) formation on the insulating layer of nano-structures based on a second semi-conductor material, from stable seeds of the first semi-conductor material by chemical deposition from a second precursor gas for the second semi-conductor material, b) being carried out over a period of exposure to the second precursor gas, selected depending on the desired predetermined size or size range of the nano-structures.

5. Method according to claim 4, with the second precursor being different to the first precursor.

6. Method according to claim 4, wherein the first semi-conductor material and the second semi-conductor material are the same.

7. Method for fabricating several Haze noise standards comprising: the fabrication of at least one first standard and at least one second standard respectively, by a method according to claim 4 with the first standard and the second standard having equal densities of nano-structures, with the first standard comprising nano-structures of a first size or associated with a first range of sizes and with the second standard comprising nano-structures of a second size which is different to the first size or associated with a range of sizes which is different to the first range.

8. Method according to claim 7, with the first standard and the second standard having been placed during a), at the same time and over the same period in the same reactor or in the same deposition chamber, with the first standard and the second standard having been respectively formed at b) by exposure to the second precursor gas for a first period and by exposure to the second precursor gas for a second period which is different to the first period.

9. Method according to claim 7, with the first standard and the second standard having been exposed to the second gas during b) for a first period and for a second period respectively, with the first period having been selected depending on at least one first predetermined first value of Haze noise or at least one first predetermined range of Haze noise that the first standard is intended to measure, with the second period having been chosen depending on at least one predetermined second Haze noise value or at least one predetermined second range of Haze noise that the second standard is intended to measure.

10. Calibration method for equipment designed to use, measure, or use and measure at least one Haze noise value comprising:
    providing at least one standard obtained by the method as described in claim 4, emitting at least one light ray towards the nano-structures of said standard, after the emission, measuring at least one Haze noise value with at least one ray which is diffracted or diffused by the standard.

11. Method for fabricating several Haze noise standards which comprise an insulating thin layer and a plurality of nano-structures having a size of between 2 and 50 nanometers and which respectively have a hemi-spherical or convex bump shape and which are regularly distributed over the insulating layer comprising the fabrication of at least one first standard and at least one second standard respectively, by a method comprising:

a) the formation on at least one insulating layer of seeds made of a first semi-conducting material by chemical deposition from a first precursor gas for the first semi-conductor material, b) formation on the insulating layer of nano-structures based on a second semi-conductor material, from stable seeds of the first semi-conductor material by chemical deposition from a second precursor gas for the second semi-conductor material, wherein the first standard and the second standard have equal densities of nano-structures, with the first standard comprising nano-structures of a first size or associated with a first range of sizes and with the second standard comprising nano-structures of a second size which is different from the first size or associated with a range of sizes which is different from the first range.

12. Method according to claim 11, with the first standard and the second standard having been placed during a), at the same time and over the same period in the same reactor or in the same deposition chamber, with the first standard and the second standard having been respectively formed at b) by exposure to the second precursor gas for a first period and by exposure to the second precursor gas for a second period which is different to the first period.

13. Method according to claim 11, with the first standard and the second standard having been exposed to the second gas during b) for a first period and for a second period respectively, with the first period having been selected depending on at least one first predetermined first value of Haze noise or at least one first predetermined range of Haze noise that the first standard is intended to measure, with the second period having been chosen depending on at least one predetermined second Haze noise value or at least one predetermined second range of Haze noise that the second standard is intended to measure.

* * * * *